Figure 2:
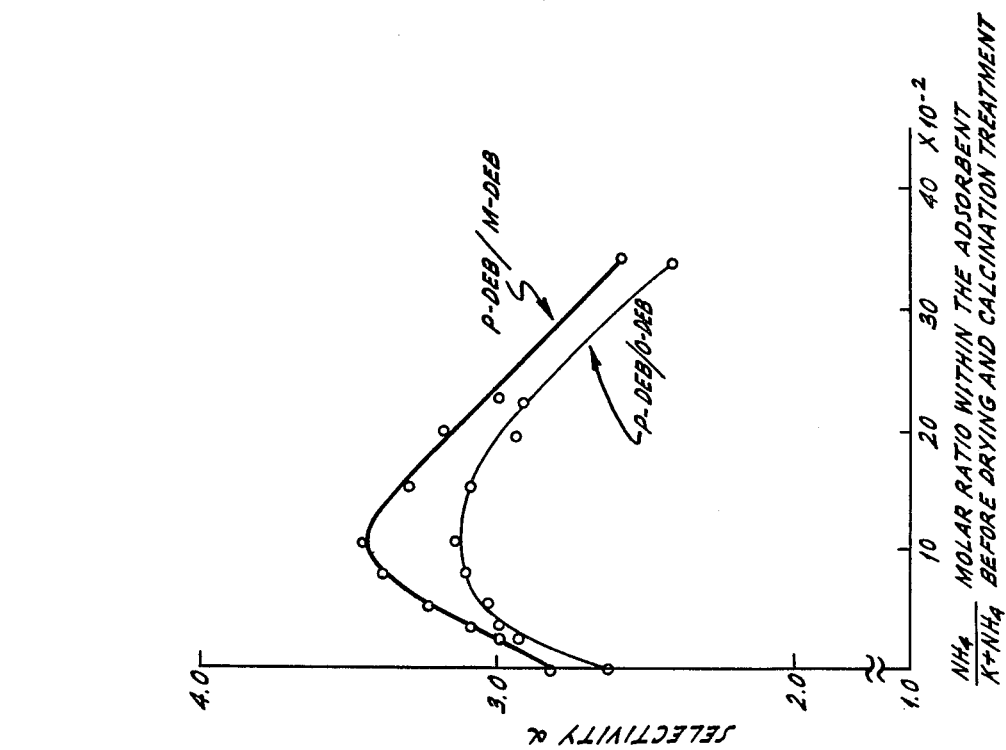

:

United States Patent [19]

Kanaoka et al.

[11] 4,069,172
[45] Jan. 17, 1978

[54] ADSORBENT FOR AROMATIC HYDROCARBON MIXTURE SEPARATION

[75] Inventors: Masazumi Kanaoka; Daisuke Ogawa; Kazuyoshi Iwayama; Makoto Kihara, all of Yokohama, Japan

[73] Assignee: Toray Industries, Inc., Nihonbashi-Muromachi, Japan

[21] Appl. No.: 667,075

[22] Filed: Mar. 15, 1976

[30] Foreign Application Priority Data

Mar. 17, 1975  Japan ................................. 50-31093

[51] Int. Cl.² .............................................. B01J 29/06
[52] U.S. Cl. ........................... 252/455 Z; 260/674 SA
[58] Field of Search .............. 252/455 Z; 260/674 SA

[56] References Cited

U.S. PATENT DOCUMENTS

| 3,644,200 | 2/1972 | Young | 208/120 |
|---|---|---|---|
| 3,647,682 | 3/1972 | Rabo et al. | 252/455 Z |
| 3,878,127 | 4/1975 | Rosback | 252/455 Z |

Primary Examiner—Carl F. Dees
Attorney, Agent, or Firm—Miller & Prestin

[57] ABSTRACT

An adsorbent for separating para-isomers from $C_8$ or $C_{10}$ aromatic hydrocarbons, specifically, a faujasite zeolite wherein about 2.5 to 25 percent, based on the total exchangeable cation sites originally present within the faujasite zeolite, is decationized and metal ions at the residual cation sites are exchanged substantially with potassium and/or barium ions. The adsorbent is used in separating the para-isomer, which is isolated by desorbing from the adsorbent.

7 Claims, 4 Drawing Figures

ADSORBENT FOR AROMATIC HYDROCARBON MIXTURE SEPARATION

BACKGROUND OF THE INVENTION

Para-xylene and para-diethylbenzene in $C_8$ or $C_{10}$ aromatic hydrocarbon mixtures are widely employed in the manufacture of synthetic fibers and also as industrial materials. The demand for para-xylene has been increasing in particular, and it relates to the demand for synthetic fibers.

Traditionally, para-xylene has been separated from $C_8$ aromatic hydrocarbon mixtures by crystallization. Recently, a new method of separation, using an adsorbent, has been disclosed. Many different kinds of adsorbents have been proposed.

DESCRIPTION OF THE PRIOR ART

For example Neuzil, in U.S. Pat. No. 3,558,730, had disclosed that para-xylene may be separated by contacting a $C_8$ aromatic mixture with faujasite zeolite containing potassium and barium ions.

Bearden et al, in U.S. Pat. No. 3,686,345, have disclosed modified Y zeolites predominantly containing potassium ions as the adsorbent for para-xylene adsorptive separation. The process for producing the adsorbent comprises 1) treating the type Y molecular sieve of the sodium form hydrothermally with an aqueous solution of an ammonium salt, to exchange 70 – 98 percent of the sodium ions with ammonium ions, 2) thermally treating under the essential presence of steam or ammonia, preferably steam, at a temperature in the range of from 315° to 760° C, to effect removal of at least some alumina tetrahedra from the crystal lattice of the zeolite, and as a result to increase the $SiO_2/Al_2O_3$ molar ratio in the zeolite and to reduce the lattice constant, 3) finally exchanging the residual sodium, ammonium and hydrogen cations with potassium ions to produce a predominantly potassium exchanged, modified Y zeolite.

However, zeolites containing only barium ions are not sufficiently selective for para-xylene adsorptive separation. The adsorbents described in Bearden U.S. Pat. No. 3,686,345 are also not sufficiently selective for para-xylene adsorptive separation, particularly for separating para-xylene from ethylbenzene in a $C_8$ aromatic hydrocarbon mixture.

We have disclosed, in Japanese patent publication Sho 48-66583, that certain adsorbents are selective for para-xylene adsorptive separation. These adsorbents are made by treating faujasite zeolite with an aqueous solution of an ammonium compound to exchange metal ions at cation sites with ammonium ions and then drying, calcining and finally exchanging metal ions at cation sites with potassium and/or barium ions. The adsorbent prepared in the above mentioned procedure is characterized by the fact that some of the cation sites are decationized and metal ions at the residual cation sites are exchanged with potassium and/or barium ions. The adsorbent is quite selective for para-xylene adsorptive separation. However, sometimes the degree of decationization within the adsorbent is not homogeneous and reproducibility is poor because the ammonium exchanged zeolite is dried and calcined and then is exchanged with potassium and/or barium ions.

In Japanese patent publication Sho 48-66583, we disclosed only that an adsorbent treated with an aqueous solution of an ammonium compound is more selective for para-xylene adsorptive separation. However, we failed to recognize fully that the degree of decationization within the adsorbent relates to the selectivity for use in paraxylene adsorptive separation, and that an adsorbent with a degree of decationization which falls within a critical range produces surprising results.

SUMMARY OF THE INVENTION

We now have discovered that the proper degree of decationization within the adsorbent is critical for the realization of optimum selectivity for para-isomer adsorptive separation.

It is an object of this invention to provide a faujasite zeolite adsorbent for $C_8$ or $C_{10}$ aromatic hydrocarbon adsorptive separation. It has been discovered that the adsorbent must be subjected to decationization within the range of from about 2.5 to 25 percent, based on the total exchangeable cation sites originally present, and must contain substantially potassium and/or barium ions at the residual cation sites.

The adsorbent is obtained by drying and calcining a faujasite zeolite including: (1) ammonium ions in the range of about 2.5 to 25% based on the total exchangeable cation sites originally present and, (2) ions selected from the group consisting of potassium and barium ions substantially at the residual cation sites.

The faujasite zeolite utilized in the practice of this invention may include, for example, X- or Y- type zeolites, which are represented by the following formula:

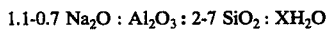

$$1.1\text{-}0.7\ Na_2O : Al_2O_3 : 2\text{-}7\ SiO_2 : XH_2O$$

Where $X = 0$ to about 9

It is well known that faujasite zeolites may be prepared by reacting hydrothermally aqueous sodium alumino-silicate which contains a silica source such as sodium silicate, silica gel, silica hydrogel, etc., an alumina source such as sodium aluminate, etc., sodium hydroxide and water.

Adsorbents in accordance with this invention can be prepared, for example, using the following method:

A faujasite zeolite may be contacted with a solution containing ammonium, potassium and/or barium ions continuously or batchwise, and most of the metal ions at the exchangeable cation sites may be exchanged with ammonium, potassium and/or barium ions.

In another ion-exchange method for preparing the adsorbent, a faujasite zeolite may be contacted with a solution containing potassium and/or barium ions continuously or batchwise and then may be contacted with an aqueous solution containing ammonium ions.

The former method is preferable to the latter, because faujasite zeolite is decationized homogeneously and preferably through the former method. According to the above mentioned procedure, faujasite zeolite is exchanged with ammonium ions and the degree of ammonium ion-exchange within the zeolite is about 2.5 to 25 percent based on the total exchangeable cation sites originally present, preferably 5 to 15 percent.

When the degree of ammonium ion-exchange within the zeolite is more than about 25 percent, the adsorptive selectivity of the para-isomer against especially ortho- and meta-isomers becomes lower than that of an adsorbent having a degree of ammonium ion-exchange of about 2.5 to 25 percent. When the degree of ammonium ion-exchange is about 2.5 to 25 percent based on the total exchangeable cation sites originally present, the adsorbent gives sharply improved selectivity for para-isomer adsorptive separation. After treating with ion-exchange solution, the zeolite may be preferably washed with water. The zeolite having been subjected to the ion-exchange treatment contains a large amount of water therein, and therefore ordinarily must be subjected to hydration so as to be activated. Accordingly, the zeolite is dried at a temperature in the range of from about 50° to 250° C, preferably from about 100 to 200° C for about 0.1 to 10 hours, preferably about 0.2 to 2.0 hours, and is then calcined at a temperature in the range of from about 300° to 700° C, preferably from about 400° to 600° C for 0.1 to 10 hours, more preferably about 0.2 to 1.0 hour. The following phenomena in an ammonium-exchanged zeolite may occur through drying and calcination:

1. deammoniation — this refers to the removal of ammonium ions as ammonia, that is, preparation of a hydrogen ion exchanged zeolite.
2. dehydroxylation — this refers to the elimination of hydroxyl groups as water, that is, preparation of decationized zeolite.

These phenomena may overlap somewhat in the drying and calcination process. In accordance with this, we define both or either of the above mentioned two phenomena as "decationization" for the sake of convenience.

Ammonium compounds utilized in the ion-exchange treatment may include ammonium hydroxide, ammonium nitrate, ammonium chloride, ammonium sulfate, ammonium phosphate, ammonium carbonate, ammonium acetate, ammonium bromide, ammonium iodide, ammonium tartrate, ammonium nitrite, etc. Amongst these, ammonium nitrate, ammonium chloride and ammonium sulfate are most preferable.

The solvent to be used is preferably water.

In treatment with an ammonium ion-exchange solution, the concentration of ammonium compounds is preferably about 1/100 to 20 mol/l.

Compounds to be used in potassium and/or barium ion-exchange treatment may include, for example, potassium or barium salts of inorganic acids such as nitric acid, carbonic acid and hydrochloric acid, metal hydroxides, and other inorganic compounds. An organic salt such as an acetate may also be used. Amongst these, nitrates, chlorides and carbonates are most preferably. These salts may be utilized as solutions in any concentrations, but in the case of an aqueous solution, the concentration by weight is preferably 1 to 20 percent and most preferably 5 to 10 percent.

The ion-exchange reaction may be effected satisfactorily even at room temperature, but is preferably conducted at an elevated temperature to increase the reaction rate. The required period for the ion-exchange treatment may be dependent upon the ammonium, potassium and barium compounds, but ordinarily may be satisfactorily less than 20 hours in a continuous method using a solution which contains ammonium, potassium and/or barium ions. In the case of a batch method using a solution which contains ammonium, potassium and/or barium ions, the solution/zeolite ratio may satisfactorily be maintained at 1 to 20 l/kg and the treatment may satisfactorily be conducted 2 to 20 times, preferably 8 to 15 times. Each treatment period per treatment time may satisfactorily be less than 120 minutes, preferably 10 to 20 minutes. When the ion exchange treatment with ammonium ions is performed batchwise after completion of the potassium and/or barium ion-exchange treatment, the solution/zeolite ratio may preferably be about 1 to 20 l/kg and the treatment may preferably be performed one to 3 times. It is undesirable to treat the zeolite excessively with ammonium solution, beyond the above mentioned ranges, because the degree of ammonium exchange within the zeolite is over 25 percent. When the zeolite is contacted with a solution containing potassium and/or barium ions before effecting the ammonium ion-exchange, the method of treatment may be performed continuously or batchwise. When the ion-exchange treatment is performed batchwise, it is preferable to repeat the treatment one to 20 times with a solution/zeolite ratio of 1 to 20 l/kg.

A lower level of residual sodium ions within the adsorbent may be more preferable. It is especially desirable that the residual sodium ions be less than 0.15 equivalent within the zeolite. The preferred ratio of barium to potassium within the adsorbent may depend upon the $SiO_2/Al_2O_3$ molar ratio of faujasite zeolite. The effect of barium ion-exchange is outstanding when the faujasite zeolite has a low $SiO_2/Al_2O_3$ molar ratio.

A faujasite zeolite adsorbent is ordinarily molded in an optimum particle size before or after ion-exchange treatment, for use industrially. The adsorbent may be molded with or without a binder. However, it is preferable that the adsorbent be molded with a binder such as bentonite, kaolin, alumina sol, silica sol, etc. to aid in maintaining adsorbent particle strength.

In use, the adsorbent is contacted with a feed mixture, using an apparatus such as a fixed bed or a fluidized bed, etc. Feed stocks which can be used in the process of this invention include either $C_8$ aromatic hydrocarbons, $C_{10}$ aromatic hydrocarbons, or mixtures thereof. The $C_8$ aromatic hydrocarbons include paraxylene, ortho-xylene, meta-xylene and ethylbenzene. The $C_{10}$ aromatic hydrocarbons include para-diethylbenzene, ortho-diethylbenzene, meta-diethylbenzene and butylbenzene, etc.

The para-isomer which is adsorbed by contacting the feed mixture with the adsorbent in accordance with this invention is separated by desorption from the adsorbent. Desorbents which can be used for para-xylene adsorptive separation in the process of this invention include benzene, toluene, any isomer or a mixture of para-, meta- or orthodiethylbenzene, tri-methylbenzene. thiophene, etc. For para-diethylbenzene adsorptive separation they include benzene, toluene, any isomer or a mixture of para-, meta-, ortho-xylene and ethylbenzene, tri-methylbenzene and thiophene, etc.

Measurement of ammonium ion content within the adsorbent may be performed by Kjeldahl analysis using an adsorbent before drying and calcination treatment. Measurement of metal ion content within the adsorbent may be performed by flame spectrum analysis or atomic adsorptive analysis.

In adsorptive separation processes, the criterion used to determine the capability of a particular adsorbent for separating components of a feed is the selectivity ($\alpha$) of the adsorbent for one component as compared to another component. The selectivity ($\alpha$) is defined by the following formula:

$$\alpha_{A/B} = C_{SA}/C_{SB} \cdot C_{LB}/C_{LA}$$

wherein $C_{SA}$ and $C_{SB}$ are concentrations of components A and B in the sorbed phase respectively, and $C_{LA}$ and $C_{LB}$ are concentrations of components A and B in the liquid phase which are in equilibrium with the sorbed phase.

As can be seen, where the selectivity of two components approaches unity there is no preferential adsorption of one component by the adsorbent. As the value of $\alpha_{A/B}$ becomes less than or greater than unity, there is a preferential selectivity by the adsorbent of one component. When comparing the selectivity of component A over component B, a valve of $\alpha_{A/B}$ greater than unity indicates preferential adsorption of component A within the adsorbent while a value of $\alpha_{A/B}$ less than unity indicates that component B is preferentially adsorbed within the adsorbent.

In testing various adsorbents, in the Examples which follow, selectivity was determined using a static testing apparatus and procedure which will now be described. The static testing apparatus had a volume 5 ml and is made of stainless steel. Feed and adsorbent were put into the apparatus and it was stoppered and placed into an oil bath at a temerature of 175° C for 1 hour. After equilibrium adsorption, the liquid in the apparatus was sampled with a microsyringe and analyzed with gas chromatography. The selectivity $\alpha_{A/B}$ was calculated according to the formula defined previously herein.

The following Examples are illustrative:

EXAMPLE 1

A total of 80 grams of sodium form type Y zeolite, molded in particle size 10 - 40 mesh, was subjected to ion-exchange treatment with an aqueous solution which contained potassium chloride and ammonium chloride, at room temperature and at a rate of 100 ml/hr continuously, until the residual sodium ion concentration within the zeolite dropped to less than 0.05 equivalent. To prepare various adsorbents, ammonium chloride concentrations in ion-exchange aqueous solutions were varied under a constant concentration of potassium chloride of 5.0 wt.%. After completing the ion-exchange treatment, the adsorbent was dried at 120° C for one hour and then calcined at 500° C for 1 hour.

Figure 1:
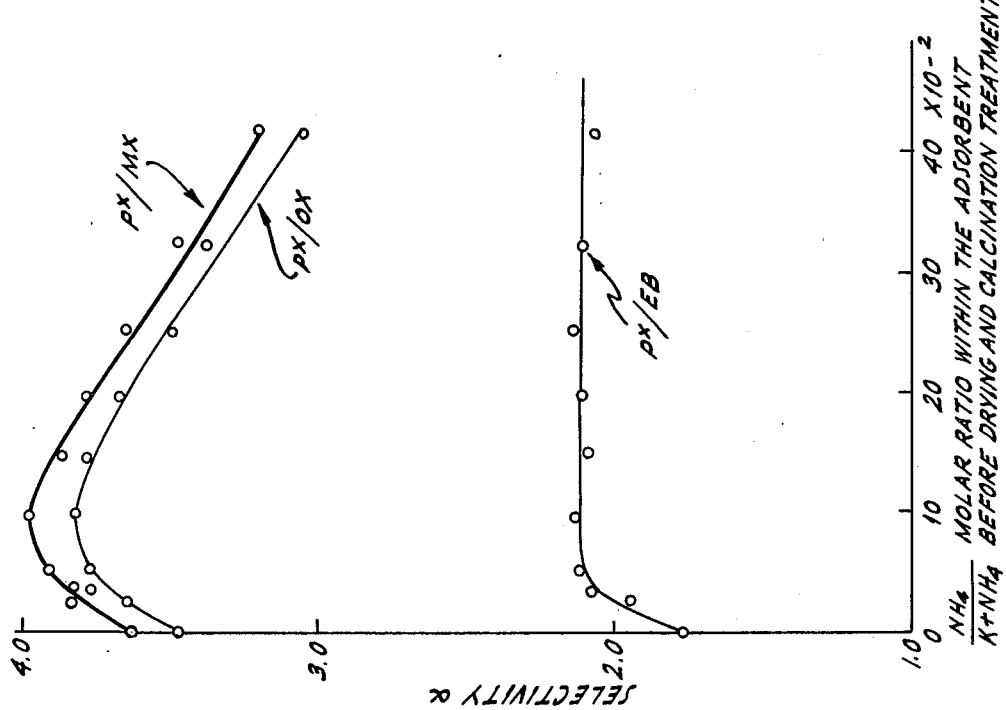

Each of these adsorbents was contacted with a feed mixture having the following composition:

normal nonane (n-C$_9$) : para-xylene (PX) :
meta-xylene (MX) : ortho-xylene (OX) :
ethylbenzene (EB) = 1:1:1:1:1 (wt. ratio)

using the method previously described. Upon the supposition that n-C$_9$ was not adsorbed within the adsorbent, the selectivity $\alpha$ was calculated using the before-mentioned formula. The results are described in FIG. 1. It can be seen from FIG. 1 that the adsorbents ion-exchanged partially with ammonium ions, that is, those which were subjected to decationization partially are more selective for para-xylene adsorptive separation.

EXAMPLE 2

Various adsorbents were prepared using the same method described in Example 1. Each of the adsorbents was contacted with a feed mixture having the following composition:

normal nonane (n-C$_9$) : para-diethylbenzene (P-DEB) :
meta-diethylbenzene (M-DEB) : ortho-diethylbenzene
(O-DEB) = 2:3:6:1.

using the method previously described. The selectivity $\alpha$ was calculated using the before-mentioned method. The results are described in FIG. 2. It can be seen also from FIG. 2 that the adsorbents which were ion-exchanged partially with ammonium ions, that is this that were subjected to decationization partially, are more selective for para-diethylbenzene adsorptive separation.

EXAMPLE 3

In this Example, comparisons were made between selectivities of three kinds of adsorbent — adsorbent containing potassium ions, adsorbent containing potassium and barium ions, and partially decationized adsorbent containing potassium and barium ions. The adsorbent containing potassium ions was prepared by continuously contacting sodium Y zeolite with an aqueous solution containing 5.0 wt.% of potassium nitrate. The adsorbent containing potassium and barium ions were prepared by contacting sodium Y zeolite with an aqueous solution containing 5.0 wt.% of each of potassium nitrate and barium chloride. The partially decationized adsorbent containing potassium and barium ions was prepared by contacting sodium Y zeolite with an aqueous solution containing 0.67 wt.% of ammonium chloride, 5.0 wt.% of potassium nitrate and 5.0 wt.% of barium chloride.

Each of these adsorbents was contacted with a feed mixture having the following composition:

n-C$_9$ : PX : MX : OX : EB = 1:1:1:1:1 with the use of the before-mentioned method, and selectivity was calculated. The results are described in Table 1.

TABLE 1

| Cations within the adsorbent | Treatment with ammonium ions | Selectivity ($\alpha$) PX/EB | PX/MX | PX/OX |
|---|---|---|---|---|
| K | No | 1.77 | 3.64 | 3.46 |
| K, Ba | No | 1.86 | 4.87 | 3.99 |
| K, Ba | Yes | 2.05 | 5.07 | 4.68 |

It can be seen that the adsorbent treated with ammonium ions, that is, the partially decationized adsorbent, is more selective for para-xylene adsorptive separation.

EXAMPLE 4

In this Example, investigations were made of the ion-exchange equilibrium relations between concentrations of ammonium, potassium and/or barium ions in ion-exchange aqueous solution and concentrations of those ions within the adsorbent.

A total of 100 grams of sodium Y zeolite were formed as a bed in a glass tube having a 12 mm inside diameter and 1,000 mm length, and an aqueous solution containing ammonium and potassium ions was fed into the bed at the rate of 150 ml/hour for 2 hours at room temperature. After the ion-exchange treatment, the contents of ammonium and potassium ions within the adsorbent were analyzed. Several different ion-exchange aqueous solutions, with various NH$_4$/K + NH$_4$ molar ratios, were prepared at a constant potassium nitrate concentration of 5.0 wt.%, and ion-exchange treatments were performed with the use of the above mentioned method. The results are described in FIG. 3.

It is shown that the zeolite should be exchanged with a solution having the following composition range:

$$\frac{NH_4}{K + NH_4} \times 100 = 8 \text{ to } 45 \text{ mole percent}$$

for preparing an adsorbent with potassium ions and with a degree of ammonium ion-exchange, that is, a degree of decationization in the range of from 2.5 to 25% based on the total exchangeable cation sites originally present.

Figure 4:
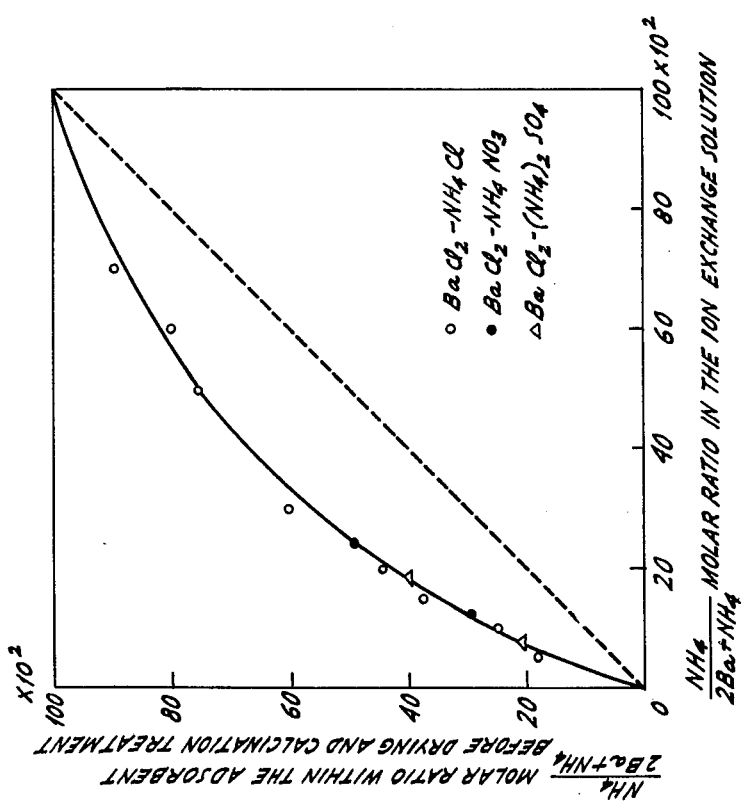

In the same manner, the zeolite was treated with a solution containing ammonium and barium ions. The results are shown in FIG. 4 of the drawings. It can be seen from FIG. 4 that the zeolite should be exchanged with a solution having the following composition range:

$$\frac{NH_4}{2Ba + NH_4} \times 100 = 1 \text{ to } 10 \text{ mole percent}$$

for preparing an adsorbent with barium ions and with a degree of ammonium ion-exchange, that is, a degree of decationization in the range of from 2.5 to 25% based on the total exchangeable cation sites originally present.

Figure 3:
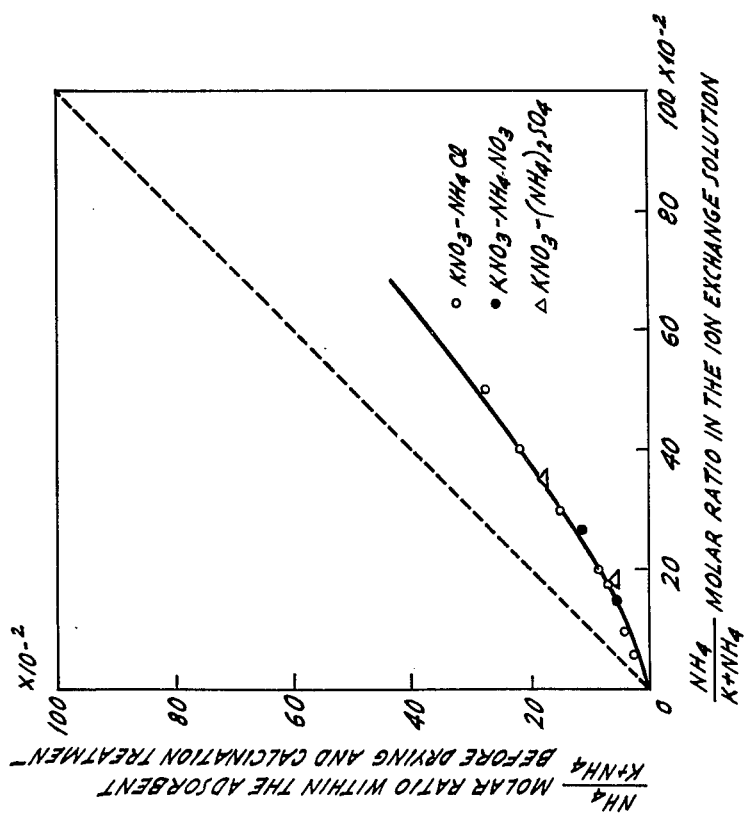

In case of treatment with a solution containing ammonium, potassium and barium ions, the ion-exchange equilibrium relation should be within the range of from FIG. 3 to FIG. 4. In other words, the zeolite should be exchanged with a solution having the following composition range:

$$\frac{NH_4}{K + 2Ba + NH_4} \times 100 = 1 \text{ to } 45 \text{ mole percent}$$

for preparing an adsorbent with potassium and barium ions and with a degree of ammonium ion-exchange, that is, a degree of decationization, in the range of from 2.5 to 25%.

Although this invention has been described with reference to specific forms and procedures, it will be appreciated that various modifications may be made, including substitution of equivalent substances and methods, the use of certain features independently of others, and the reversal of certain steps of the method, all within the spirit and scope of the invention as defined in the appended claims.

We claim:

1. An adsorbent for separating paraisomers from $C_8$ or $C_{10}$ aromatic hydrocarbons, or mixtures thereof, which is obtained by drying and calcining a faujasite zeolite including: (1) ammonium ions in the range of 2.5 to 25%, based on the total exchangeable cation sites originally present, and (2) ions selected from the group consisting of potassium and barium ions at the residual cation sites.

2. The adsorbent according to claim 1, wherein said ammonium ions are present in the range of about 5 to 15 percent.

3. The adsorbent according to claim 1, wherein said initial faujasite zeolite contained substantial concentrations of sodium ions, and wherein the residual sodium content within said adsorbent is less than about 0.15 equivalent.

4. The adsorbent according to claim 1, wherein said para-isomer is para-xylene or para-diethylbenzene.

5. The adsorbent defined in claim 1, wherein said initial faujasite type zeolite is selected from the group consisting of X- and Y- type zeolites.

6. The adsorbent defined in claim 5, wherein said initial faujasite type zeolite contains oxides of sodium, aluminum and silica according to the formula

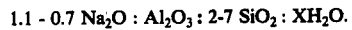

1.1 - 0.7 $Na_2O$ : $Al_2O_3$ : 2-7 $SiO_2$ : $XH_2O$.

7. The adsorbent defined in claim 6, wherein said zeolite is molded into particles with a binder selected from the group consisting of bentonite, kaolin, alumina sol and silica sol.

* * * * *